DEFENSIVE PUBLICATION

UNITED STATES PATENT AND TRADEMARK OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent and Trademark Office makes no assertion as to the novelty of the disclosed subject matter.

PUBLISHED OCTOBER 7, 1975

939 O.G. 7

T939,003

METHOD FOR SYNTHESIS OF 1-FORMYL-2-(P-TOLYL) HYDRAZINE

Cataldo A. Maggiulli and Richard J. Schottmiller, both of 1669 Lake Ave., Rochester, N.Y. 14650

Filed Aug. 13, 1973, Ser. No. 387,824

Int. Cl. C07c *103/30*

U.S. Cl. 260—562 H

No Drawing. 10 Pages Specification

1-Formyl-2-(p-tolyl)hydrazine has been synthesized directly from p-tolylhydrazine hydrochloride and formamide by a single, one-step method which comprises reacting the p-tolylhydrazine hydrochloride at an elevated temperature in the range of about 40° C. to 70° C. with formamide in the presence of water and a lower alkanoic acid. The synthesis may be represented by the following formula:

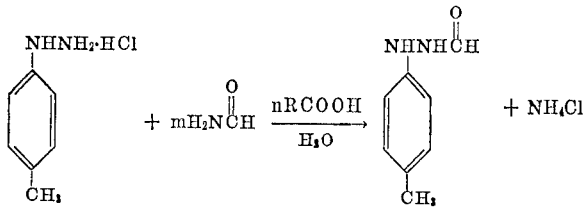

wherein R is a hydrogen atom or an alkyl having 1 to 5 carbon atoms, *m* is a number greater than 1, preferably about 2, and *n* is a number from about 6 to about 8. The method of this invention is more advantageous than prior art methods in that it is readily adaptable to large scale production, provides increased yields, and has only one step thereby eliminating the need to isolate p-tolylhydrazine, a relatively unstable intermediate. Moreover, crude p-tolylhydrazine hydrochloride may be used in the reactions thereby eliminating a purification step.